United States Patent
Hornesby

(10) Patent No.: US 10,709,595 B2
(45) Date of Patent: Jul. 14, 2020

(54) FINGER SUPPORT ASSEMBLY

(71) Applicant: Denna Hornesby, Vallejo, CA (US)

(72) Inventor: Denna Hornesby, Vallejo, CA (US)

(*) Notice: Subject to any disclaimer, the term of this patent is extended or adjusted under 35 U.S.C. 154(b) by 375 days.

(21) Appl. No.: 15/651,867

(22) Filed: Jul. 17, 2017

(65) Prior Publication Data

US 2019/0015236 A1 Jan. 17, 2019

(51) Int. Cl.
*A61F 5/058* (2006.01)

(52) U.S. Cl.
CPC .................. *A61F 5/05875* (2013.01)

(58) Field of Classification Search
CPC .... A61F 5/05875; A61F 5/05866; A61F 5/11; A61F 5/50; A61F 2007/0037; A61F 13/10; A61F 13/104; A61F 13/105; A61F 2/42; A61F 2/4241; A61F 2/4606; A61F 2/586; A61F 2/588; A61F 2002/7856; A61F 5/0118; A61F 5/013
See application file for complete search history.

(56) References Cited

U.S. PATENT DOCUMENTS

| | | | |
|---|---|---|---|
| 4,167,044 A | 9/1979 | Girard | |
| D293,379 S | 12/1987 | Link | |
| 4,940,046 A * | 7/1990 | Jacoby | A61F 5/019 128/882 |
| 5,095,897 A | 3/1992 | Clark et al. | |
| 5,267,945 A | 12/1993 | Doctor et al. | |
| 5,346,462 A * | 9/1994 | Barber | A61F 5/05875 128/880 |
| 6,139,514 A * | 10/2000 | Benson | A61F 13/105 602/22 |
| 6,165,148 A | 12/2000 | Carr-Stock | |
| 6,183,452 B1 * | 2/2001 | Bodmer | A61F 13/068 602/11 |
| 2002/0169404 A1 * | 11/2002 | Olderr | A61F 13/068 602/41 |
| 2011/0245747 A1 * | 10/2011 | Wollstein | A61F 5/05875 602/22 |
| 2014/0188237 A1 * | 7/2014 | McCormick | A61F 5/019 623/21.19 |
| 2014/0316320 A1 * | 10/2014 | Bruckmann | A61F 5/0111 602/22 |

* cited by examiner

*Primary Examiner* — Tarla R Patel

(57) ABSTRACT

A finger support assembly for treating symptoms of a finger injury and disease includes a tube that has a finger selectively extended therethrough. The tube is comprised of a rigid material to restrain the finger thereby treating symptoms of a finger injury. A pad is coupled to the tube to enhance comfort of the finger in the tube.

1 Claim, 3 Drawing Sheets

FINGER SUPPORT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to support devices and more particularly pertains to a new support device for treating symptoms of a finger injury and disease.

BRIEF SUMMARY OF THE INVENTION

An embodiment of the disclosure meets the needs presented above by generally comprising a tube that has a finger selectively extended therethrough. The tube is comprised of a rigid material to restrain the finger thereby treating symptoms of a finger injury. A pad is coupled to the tube to enhance comfort of the finger in the tube.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
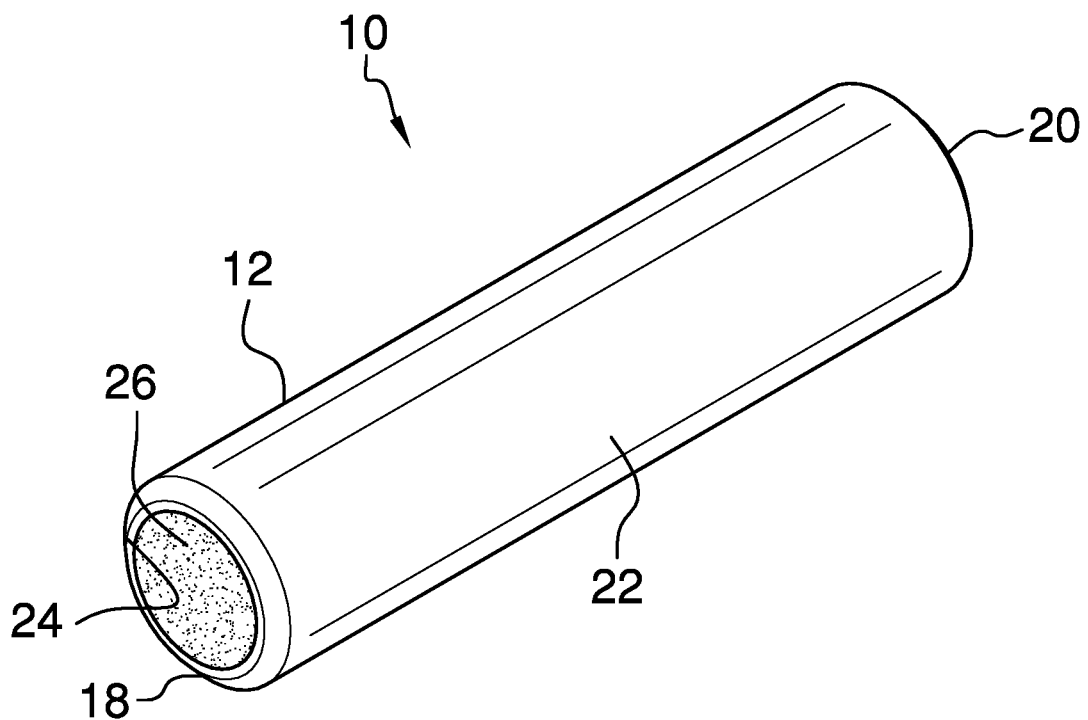
FIG. 1 is a perspective view of a finger support assembly according to an embodiment of the disclosure.
Figure 2:
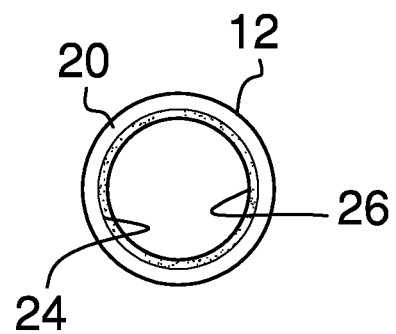
FIG. 2 is a back view of an embodiment of the disclosure.
Figure 3:
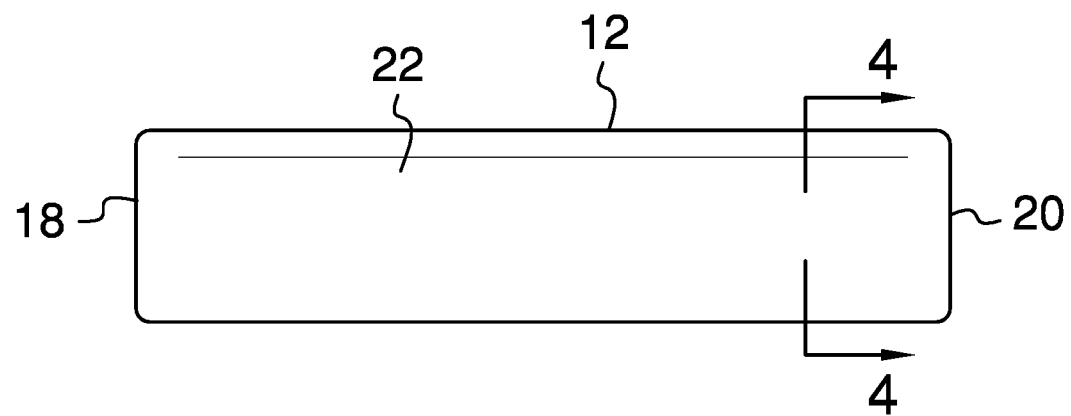
FIG. 3 is a top view of an embodiment of the disclosure.
Figure 4:
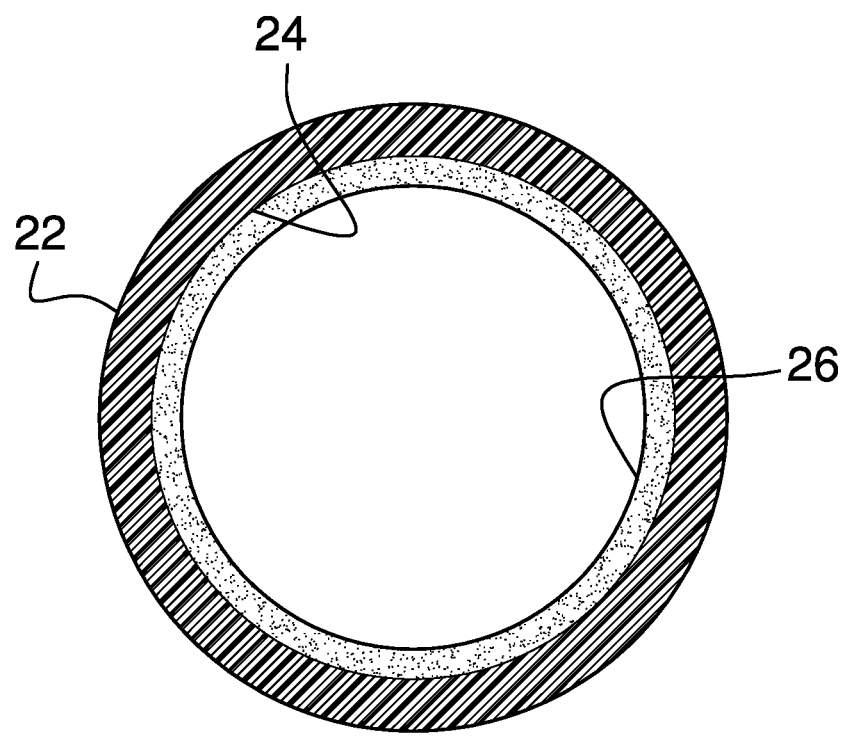
FIG. 4 is a cross sectional view taken along line 4-4 of FIG. 3 of an embodiment of the disclosure.
Figure 5:
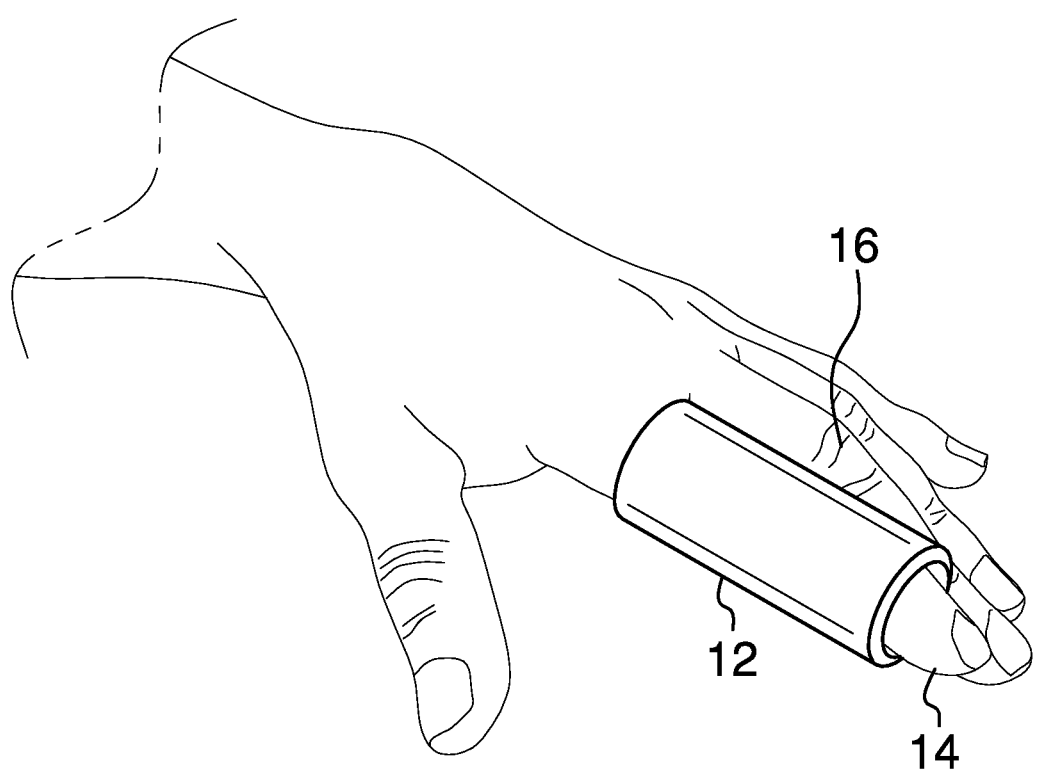
FIG. 5 is a perspective in-use view of an embodiment of the disclosure.

With reference now to the drawings, and in particular to FIGS. 1 through 5 thereof, a new support device embodying the principles and concepts of an embodiment of the disclosure and generally designated by the reference numeral 10 will be described.

As best illustrated in FIGS. 1 through 5, the finger support assembly 10 generally comprises a tube 12 that may have a finger 14 extended therethrough when the finger 14 is injured or suffering from a disease. The injury may be a sprain, a dislocation and any other finger 14 injury. The disease may be osteoarthritis, carpal tunnel syndrome, trigger finger 14 and any other joint disease.

The tube 12 has a length of at least 2.0 inches. In this way the tube 12 extends over a knuckle 16 on the finger 14 thereby inhibiting the knuckle 16 from bending. The tube 12 is comprised of a rigid material, such as plastic or the like, to restrain the finger 14 thereby treating symptoms of the finger 14 injury and disease. The tube 12 has a first end 18, a second end 20 and an outer wall 22 extending therebetween, and the outer wall 22 has an inside surface 24.

A pad 26 is coupled to the tube 12 to enhance comfort of the finger 14 in the tube 12. The pad 26 is coupled to the inside surface 24 of the tube 12 and the pad 26 completely covers the inside surface 24. The pad 26 is comprised of a resiliently compressible material, such as wool or the like, to inhibit the tube 12 from frictionally engaging the finger 14 and causing discomfort. Additionally, the pad 26 may be comprised of a thermally insulating material to keep the finger 14 warm when the tube 12 is worn on the finger 14.

In use, the tube 12 is worn on the finger 14 when the finger 14 needs to be immobilized for the treatment of the finger injury and the finger disease. The tube 12 inhibits the finger 14 from bending and potentially aggravating the injury and disease. The pad 26 cushions the finger 14 when the tube 12 is worn on the finger 14. Additionally, the pad 26 keeps the finger 14 warm when the tube 12 is warn thereby easing pain in the finger 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A finger support assembly being configured to restrain a finger for treating an injury, said assembly comprising:
   a tube being configured to have a finger extended therethrough, said tube having a length of at least 2.0 inches wherein said tube is configured to extend over a knuckle on the finger thereby inhibiting the knuckle from bending, said tube being comprised of a rigid material wherein said tube is configured to restrain the finger thereby treating symptoms of a finger injury, said tube having a first end, a second end and an outer wall extending therebetween, said outer wall having an inside surface, said outer wall being continuous between said first end and said second end; and
   a pad being coupled to said tube wherein said pad is configured to enhance comfort of the finger in said tube, said pad being coupled to said inside surface of said tube such that said pad completely covers said inside surface, said pad being comprised of a resiliently compressible material.

* * * * *